(12) United States Patent
Hu

(10) Patent No.: US 6,530,906 B2
(45) Date of Patent: Mar. 11, 2003

(54) SAFETY SYRINGE HAVING A RESTRICTIVELY ROTATABLE PLUNGER

(75) Inventor: Chien-Kung Hu, Miao Li Hsien (TW)

(73) Assignee: Taiject Medical Device Co., Ltd., Taiwan (CN)

( * ) Notice: Subject to any disclaimer, the term of this patent is extended or adjusted under 35 U.S.C. 154(b) by 0 days.

(21) Appl. No.: 09/887,175

(22) Filed: Jun. 25, 2001

(65) Prior Publication Data

US 2002/0198499 A1 Dec. 26, 2002

(51) Int. Cl.[7] .............................................. A61M 5/315
(52) U.S. Cl. ....................... 604/218; 604/186; 604/187; 128/919
(58) Field of Search ................................ 604/187, 186, 604/198, 211, 218, 110, 195, 192; 128/DIG. 1, 919

(56) References Cited

U.S. PATENT DOCUMENTS

| | | | | |
|---|---|---|---|---|
| 4,206,768 A | * | 6/1980 | Bailey .......................... 600/576 |
| 4,498,904 A | * | 2/1985 | Turner et al. ................ 422/928 |
| 4,568,335 A | * | 2/1986 | Updike et al. ............... 604/211 |
| 4,946,446 A | * | 8/1990 | Vadher ......................... 604/198 |
| 5,024,661 A | * | 6/1991 | Wender et al. ............... 604/110 |

FOREIGN PATENT DOCUMENTS

GB         2301035       * 11/1996

* cited by examiner

*Primary Examiner*—Michael J. Hayes
*Assistant Examiner*—Kathryn L. Thompson
(74) *Attorney, Agent, or Firm*—Browdy and Neimark, P.L.L.C.

(57) ABSTRACT

A safety syringe comprises a barrel having a grip lug with two fitting holes and two retaining holes communicating with each other; an elastic lashing member capable of retracting elastically and inwards, and having two locating pillars which are provided with an arresting head being retained in the retaining holes of the barrel, two slide confining portions being disposed at each side; a plunger having two slide pieces; a needle holder being caught and pulled by the plunger, and fitting a needle set. In use, the slide pieces of the plunger are confined by the slide confining portion of the elastic lashing member such that the plunger can not be turned. The plunger arrives at the bottom in the wake of injection such that the plunger is not confined by the elastic lashing member, and that the plunger can be thus turned to actuate the needle holder and drawn into the interior of the barrel by the plunger.

10 Claims, 8 Drawing Sheets

SAFETY SYRINGE HAVING A RESTRICTIVELY ROTATABLE PLUNGER

FIELD OF THE INVENTION

The present invention relates generally to a safety syringe, and more particularly to a restrictively rotatable plunger of the safety syringe.

BACKGROUND OF THE INVENTION

The conventional syringe comprises a barrel and a plunger which is disposed in the barrel in such a manner that the plunger can be turned without limitation in relation to the barrel. However, there are currently a variety of safety syringes, which comprise a restrictively rotatable plunger so as to facilitate the catching of the needle holder by the plunger. The restrictive rotation of the plunger is attained by a single control method which is limited in its application. In addition, the conventional structures are complicated in construction and can not be easily assembled. Moreover, the conventional structures do not work properly.

SUMMARY OF THE INVENTION

It is the primary objective of the present invention to provide a safety syringe with a plunger which can be turned restrictively with certainty.

It is another objective of the present invention to provide a safety syringe with a structure which is designed to enable a plunger of the safety syringe to be turned with limitation and can be easily assembled at low cost.

It is still another objective of the present invention to provide a safety syringe with a plunger rotating structure which is simple in construction and can be operated with ease.

The present invention comprises a barrel having a grip log, two fitting holes and two retaining holes; an elastic lashing member capable of retracting elastically and having two locating pillars which are provided at the top end with an arresting head. The arresting head is fitted with the fitting hole. The locating pillars are retained in the retaining holes of the barrel. Two sliding and confining portions are respectively disposed in the opposite inner sides of the bases such that they form inwardly a slide slot; a plunger having two slide pieces, a rear rod body connected with the rear segment of the front rod body, a rotation confining portion disposed at the front end thereof; a needle holder having a cooperating portion to be caught by the rotation confining portion of the plunger, a needle connection portion for fitting the needle set.

In use, the slide pieces of the plunger are confined by the slide portion of the elastic lashing member and can not be turned. Upon completion of injection, which the plunger is arrived at the bottom, the plunger is not confined by the elastic lashing member and can be thus turned to actuate the needle holder, which is then drawn into the barrel by the plunger.

DETAILED DESCRIPTION OF THE INVENTION

Figure 1:
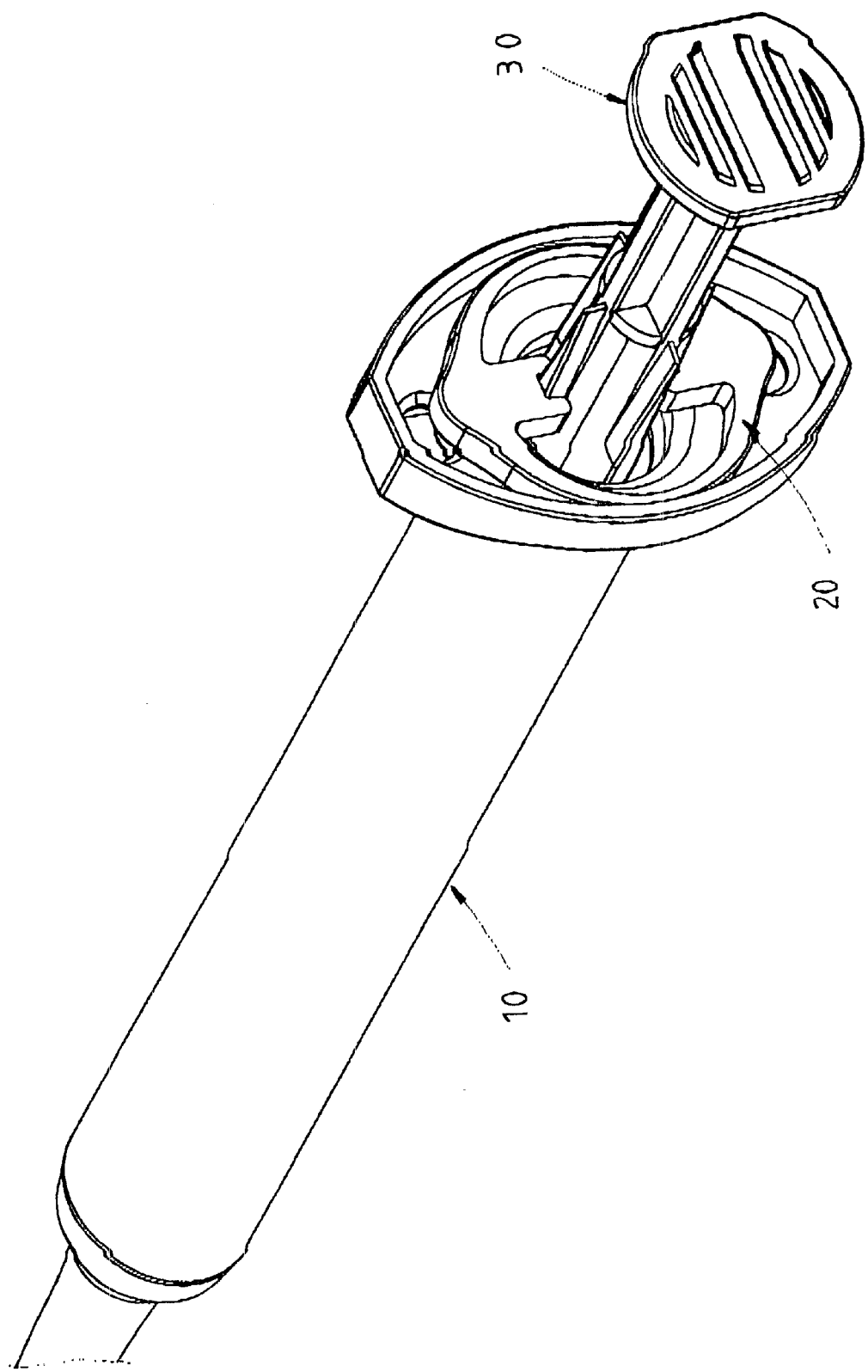
FIG. 1 shows a perspective view of a preferred embodiment of the present invention.
Figure 2:
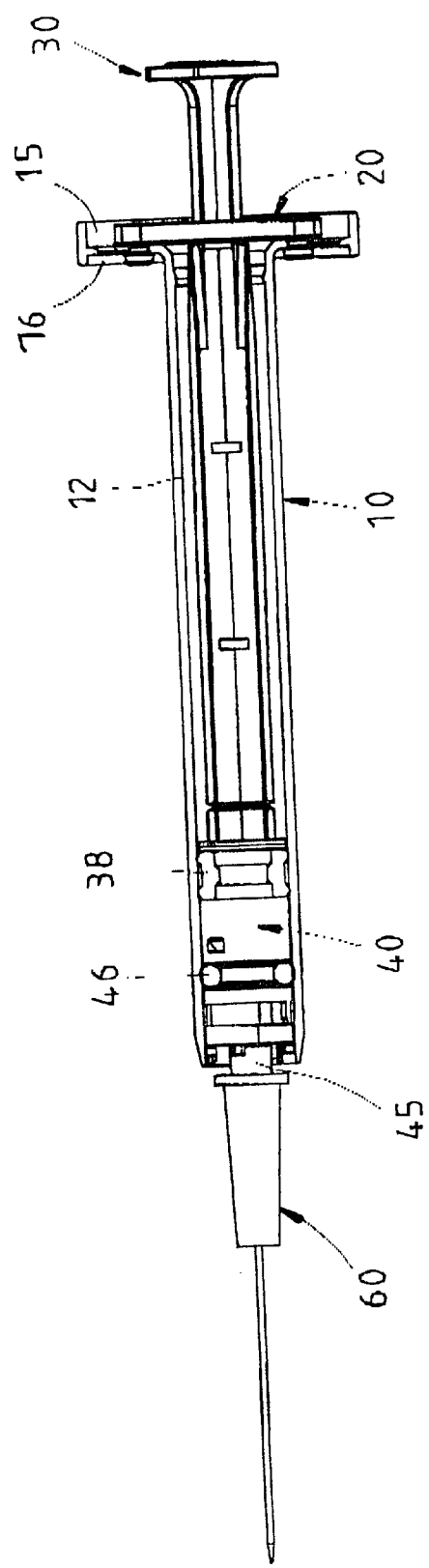
FIG. 2 shows a front sectional view of the preferred embodiment of the present invention in combination.

As shown in FIGS. 1 and 2, a safety syringe embodiment in the present invention is provided with a needle set 60 fitted therewith.

Figure 3:
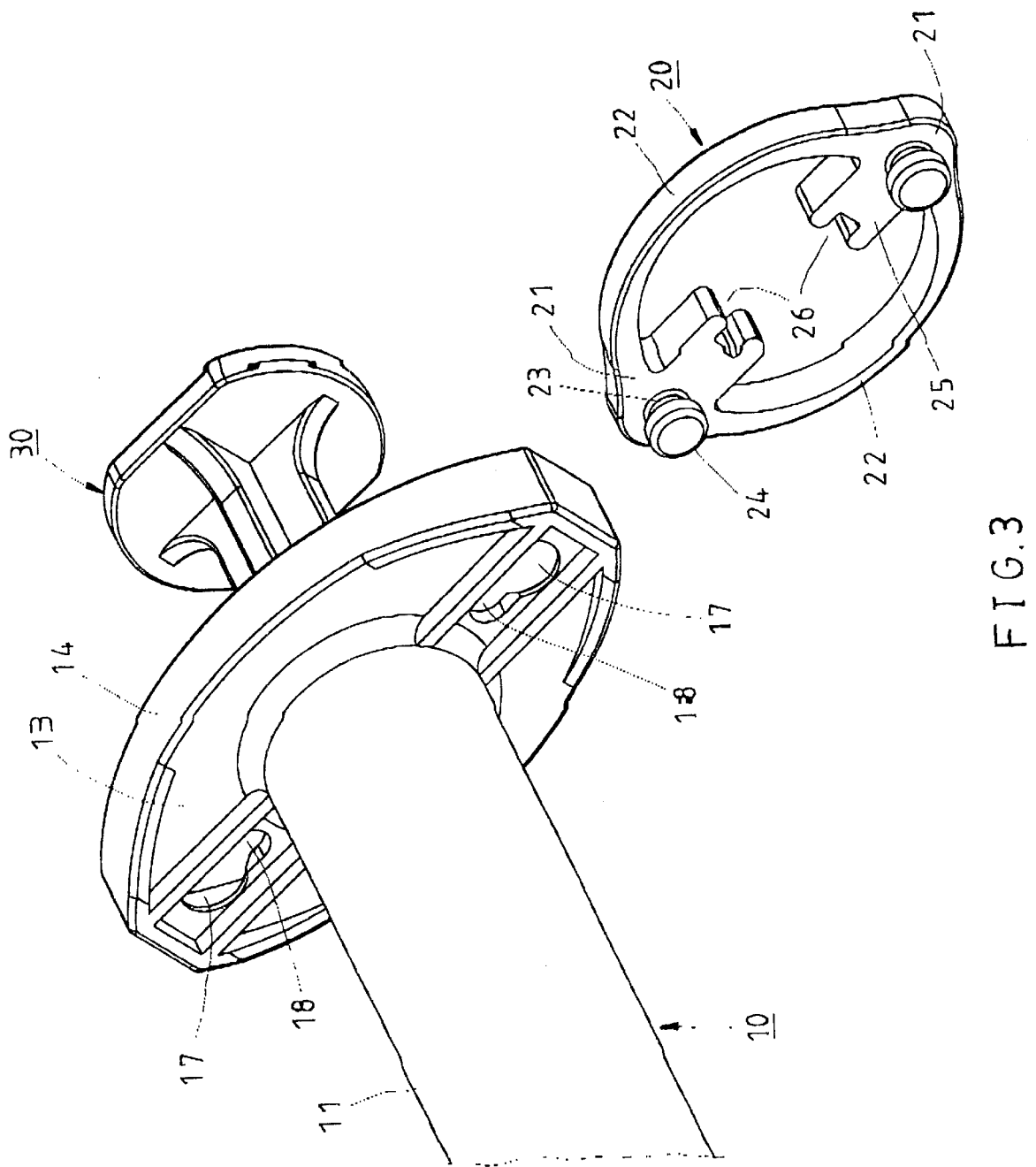
FIG. 3 is a perspective view of the preferred embodiment of the present invention to show that the elastic lashing member is in the separation state.
Figure 4:
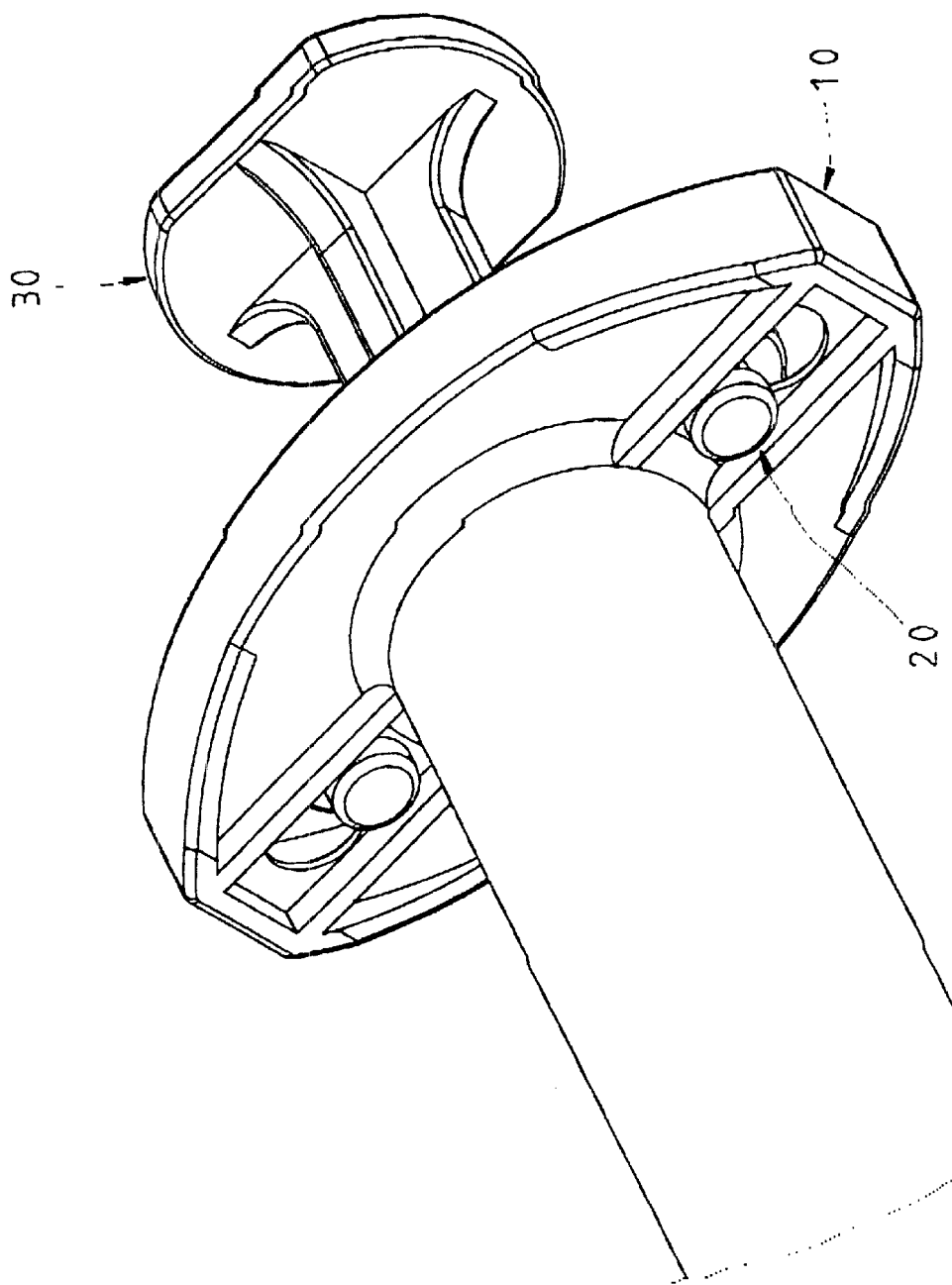
FIG. 4 shows a partial perspective view of the preferred embodiment of the present invention in combination.

As shown in FIGS. 3 and 4, the safety syringe comprises the following components parts.

A barrel 10 having a cylindrical body 11 which is provided with a receiving hole 12, a grip lug 13 disposed at other end of the cylindrical body 11, a protective wall 14 disposed in the outer periphery of the grip lug 13 and provided with an upper recess 15 and a lower recess 16, two fitting holes 17 disposed oppositely along the direction of the longitudinal axis of the grip lug 13, two retaining holes 18 disposed in the grip lug 13 such that they are opposite to the inner sides of the fitting holes 17 and that they are slightly smaller in hole diameter than the fitting holes 17, a rotating confining portion 19 disposed at a predetermined position of the front end thereof.

An elastic lashing member 20 is disposed in the upper recess 15 of the barrel 10 and is circular shape. The lashing member 20 has two bases 21 and two arcuate elastic portions 22 enabling the bases 21 to retract elastically toward opposite inner sides, two locating pillars 23 provided with an arresting head 24 and connected with the underside of each base 21. The arresting head 24 is fitted with the fitting hole 17 of the barrel 10. The locating pillar 23 is retained in the retaining hole 18 of the barrel 10. Two sliding confining portions 25 are disposed in the opposite inner sides of the bases 21 and are provided with a sliding confining slot 26 extending inwardly.

A plunger 30 has a front rod body 31 which is received in the receiving hole 12 of the barrel 10 and is provided with four slide pieces 32 which are provided in the axial outer periphery with a pointed slide-in plate 33, a rear rod body 34 connected with the rear segment of the front rod body 31, a press head 35 connected with rear rod body 34, a catching and turning portion 36 disposed at the front end thereof, a breaking portion 37. Then further providing a stopper 38 disposed at the front end thereof to seal off the receiving hole 12 of the barrel 10.

A needle holder 40 is disposed in the receiving hole 12 of the barrel 10 and is provided with a rotation confining cooperating portion 43 corresponding to the rotation confining portion 19, a catching turning cooperating portion 44 formed at the rear end to be caught and pulled by the catching and turning portion 36 of the plunger 30, a needle connection portion 45, and an O-ring 46 fitted on the outer circumference.

In combination, the elastic lashing member 20 can be elastically deformed by the deforming or elongating the elastic portions 22, thereby causing the bases 21 to extend outwards and oppositely so as to enable two arresting heads 24 thereof to be put through the fitting holes 17 of the barrel 10. As the elastic portions 22 are let go, the bases 21 retract inwards and elastically such that their locating pillars 23 are retained in the retaining holes 18 of the barrel 10, and that the elastic lashing member 20 is prevented by the arresting heads 24 from slipping out.

Figure 5:
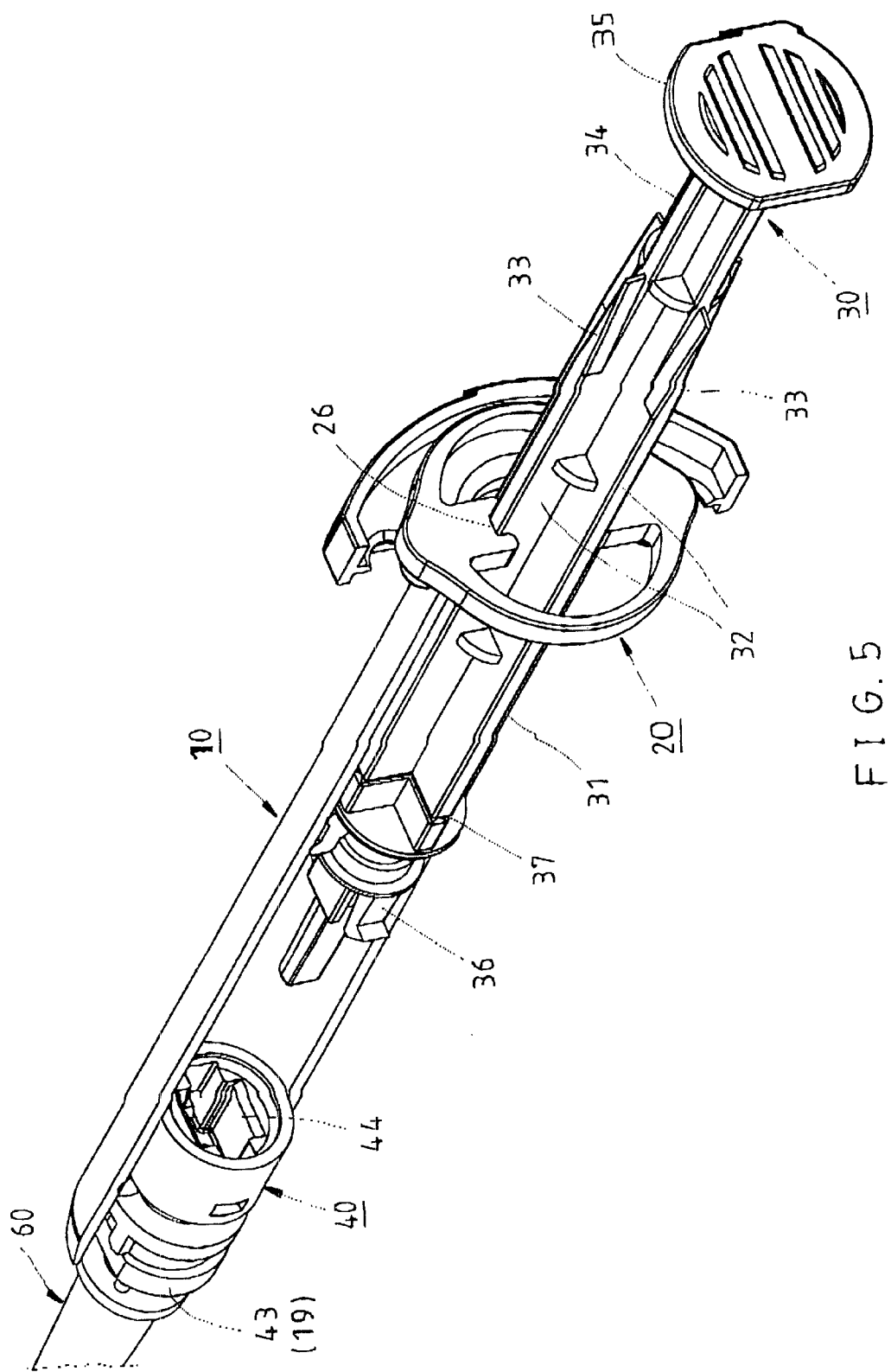
FIG. 5 is a sectional view of the preferred embodiment of the present invention to show that the plunger is in the confinement state in the course of its injection stroke.

In operation, as shown in FIG. 5, the two slide pieces 32 of the plunger 30 are disposed in the slide confining slot 26 of the elastic lashing member 20 such that the two slide pieces 32 are capable of sliding restrictively. As a result, the plunger 30 can not be turned in relation to the barrel 10.

Figure 6:
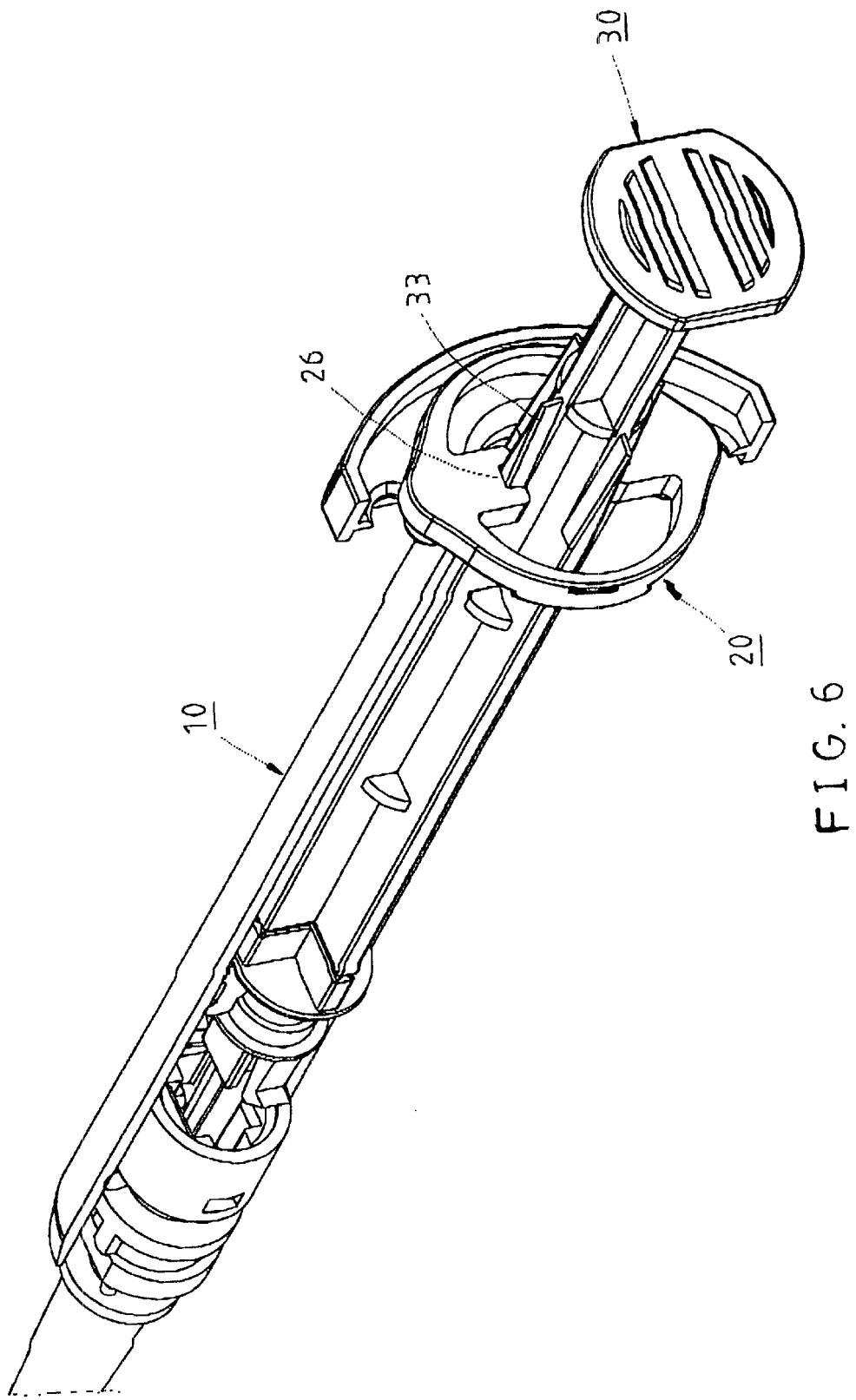
FIG. 6 is a sectional view of the preferred embodiment of the present invention to show that the plunger is in the state of sliding into or out in relation to the elastic lashing member.

As shown in FIG. 6, the plunger has almost arrived at the end of its stroke such that the slide confining slot 26 of the elastic lashing member 20 is confined at the position of the pointed slide-in plate 33 of the plunger 30. The plunger 30 still can not be turned.

Figure 7:
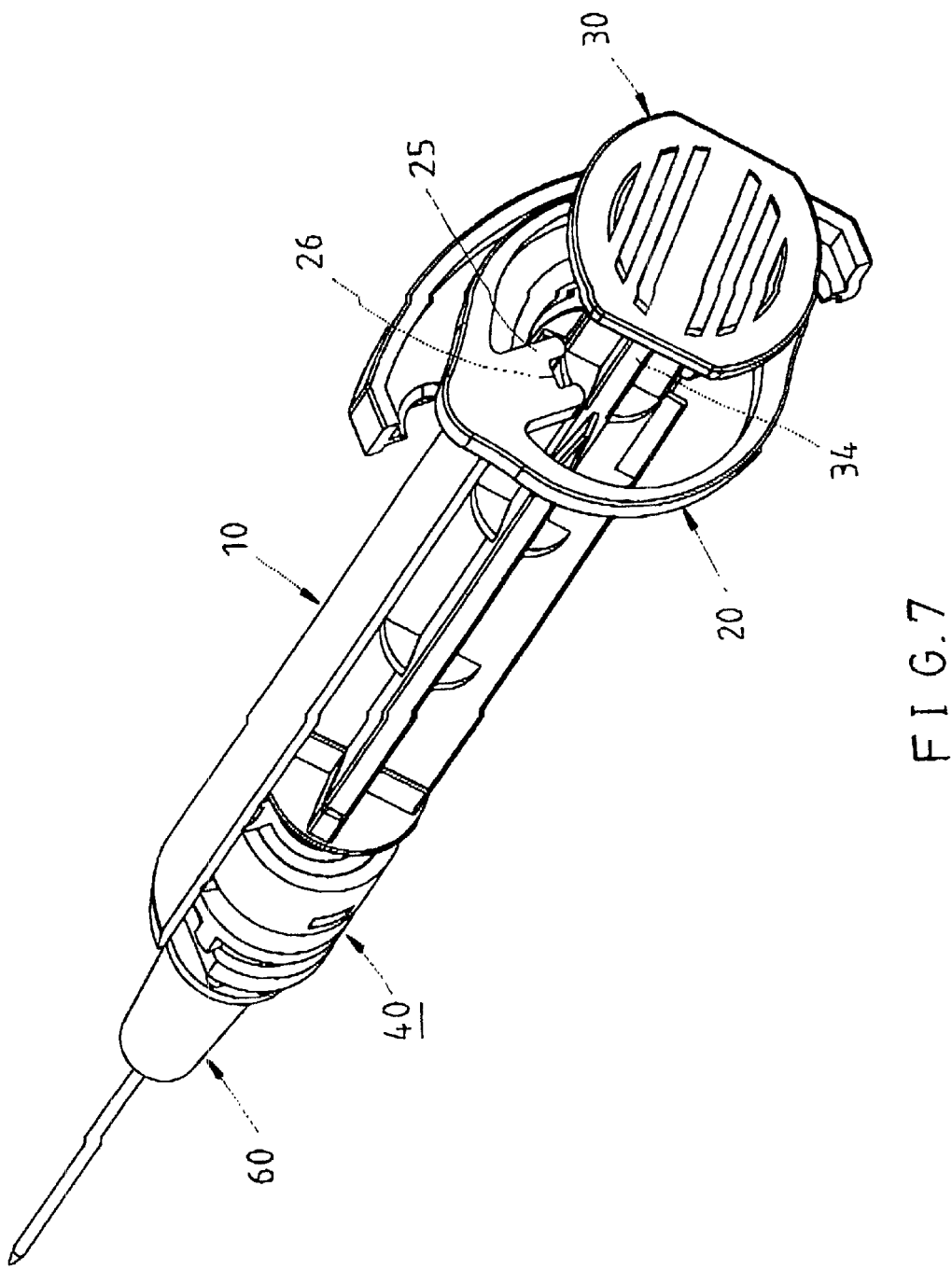
FIG. 7 is a sectional view of the preferred embodiment of the present invention to show that the needle holder is caught and turned by the plunger in the wake of injection.

As shown in FIG. 7, the injection is completed such that the catching and turning portion 36 of the plunger 30 is corresponding to the catching turning cooperating portion 44 of the needle holder 40, and that the rear rod body 34 is located in location to the elastic lashing member 20, without being confined by the slide confining slot 26. The slide pieces 32 of the plunger 30 are not confined by the slide confining slot 26 of the elastic lashing member 20. Then the plunger 30 can be turned a predetermined angle in relation to the barrel 10.

Figure 8:
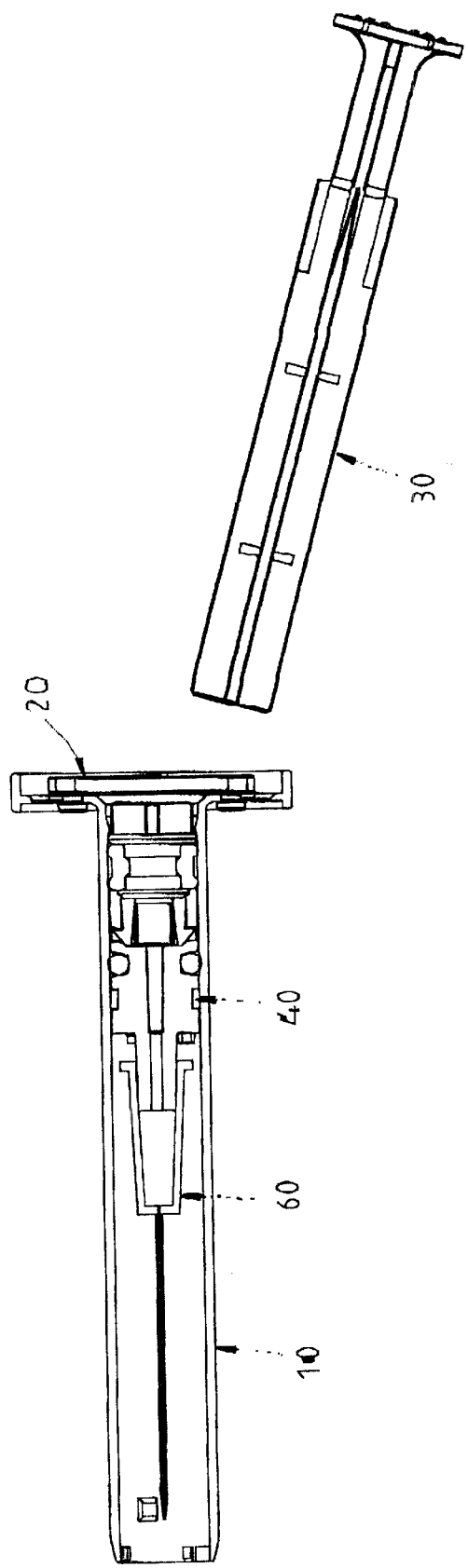
FIG. 8 is a top sectional view of the preferred embodiment of the present invention to show that the needle holder is drawn back in and that the plunger is broke.

As shown in FIG. 8, the needle holder 40 turns the barrel 10 such that the confining turning cooperating portion 43 is separated from the rotation confining portion 19 of the barrel 10. The needle holder 40 can be caught and pulled by the plunger 30, thereby actuating the needle set 60 to retract rearwards into the receiving hole 12 of the barrel 10. The plunger 30 can be broke at the breaking portion 37 thereof to prevent the needle holder 40 and the needle set 60 from being pushed out.

The present invention has advantages over the prior art. In the first place, the sliding motion of the plunger of the present invention is confined by the elastic lashing member, thereby restricting the plunge to be turned or not to be turned in relation to the barrel. In addition, the confining members of the present invention are simple in design and assembly, and work reliably.

What is claimed is:

1. A safety syringe comprising:

a barrel having a cylindrical body, a receiving hole, a grip lug fastened to a rear end of said cylindrical body, two fitting holes disposed oppositely in the direction of a longitudinal axis of said grip lug, two retaining holes disposed in said grip lug and opposite to inner sides of said fitting holes and in communication with said fitting holes;

an elastic lashing member disposed in said grip lug of said barrel and provided with an elasticity enabling said lashing member to retract inwards, two locating pillars fixed on bases of the lashing member having at a free end thereof an arresting head, said arresting head being disposed in said fitting hole of said grip lug, said locating pillars being retained in said retaining holes, two slide confining portions being disposed in opposite inner sides of said bases and provided with a slide confining slot extending inwards;

a plunger having a front rod body which is inserted into said receiving hole of said barrel and is provided in axial outer periphery thereof with two slide pieces, a rear rod body connected with a rear segment of said front rod body, a press portion connected with said rear rod body, a catching and turning portion disposed at a front end of said front rod body;

a needle holder disposed in said receiving hole of said barrel and provided with a catching turning cooperating portion located at a rear end thereof to be caught and pulled by said catching and turning portion of said plunger, a needle connection portion for fitting said needle set;

said slide pieces of said plunger being confined by said slide confining portion of said elastic lashing member such that said plunger cannot be turned at the time when said syringe is in use, said plunger arriving at a bottom in the wake of injection such that said plunger is not confined by said elastic lashing member, and that said plunger can be thus turned to actuate said needle holder, thereby enabling said needle holder to be drawn into an interior of said barrel by said plunger.

2. The safety syringe as defined in claim 1, wherein said barrel further has a protective wall which is disposed at the outer periphery of said grip lug.

3. The safety syringe as defined in claim 1, wherein said barrel is further provided in said grip lug thereof with an upper recess for receiving said elastic lashing member.

4. The safety syringe as defined in claim 1, wherein said retaining holes of said barrel are smaller in hole diameter than said fitting holes.

5. The safety syringe as defined in claim 1, wherein said barrel is further provided at the front end with a rotation confining portion; wherein said needle holder is provided with a confining turning cooperating portion corresponding to the needle holder rotation confining portion of said barrel.

6. The safety syringe as defined in claim 1, wherein said elastic lashing member is formed of two bases and two arcuate elastic portions connected with each other.

7. The safety syringe as defined in claim 6, wherein said two bases are caused to displace outwards and oppositely by pressing inwardly said two elastic portions of said elastic lashing member.

8. The safety syringe as defined in claim 1, wherein said plunger is provided with four slide pieces which are equiangularly arranged in the axial outer periphery thereof.

9. The safety syringe as defined in claim 1, wherein said plunger is further provided at an end of each of said slide pieces thereof with a point slide-in plate fastened therewith.

10. The safety syringe as defined in claim 1, wherein said plunger is further provided at a front end thereof with a stopper, wherein said needle holder is provided with an O-ring fitted therewith.

* * * * *